United States Patent [19]

Aldinger

[11] Patent Number: 4,704,686

[45] Date of Patent: Nov. 3, 1987

[54] METHOD OF MANUFACTURING OF INDIVIDUALLY FORMED PROTHESIS OR IMPLANT

[76] Inventor: Günther Aldinger, Engelfriedshalde 13, Tübingen, Fed. Rep. of Germany

[21] Appl. No.: 865,551

[22] Filed: May 20, 1986

Related U.S. Application Data

[63] Continuation-in-part of Ser. No. 783,794, Oct. 3, 1985, abandoned, which is a continuation of Ser. No. 484,143, Apr. 8, 1983, abandoned.

[30] Foreign Application Priority Data

Apr. 10, 1982 [DE] Fed. Rep. of Germany ....... 3213434

[51] Int. Cl.$^4$ ............................................. B23Q 15/14
[52] U.S. Cl. .................................... 364/468; 364/414; 623/16; 623/22
[58] Field of Search .................. 364/414, 468; 623/16, 623/17, 18, 19, 20, 21, 22, 23

[56] References Cited

U.S. PATENT DOCUMENTS

| | | | |
|---|---|---|---|
| 3,846,846 | 11/1974 | Fischer | 3/1 |
| 3,875,593 | 4/1975 | Shersher | 3/1 |
| 3,906,550 | 9/1975 | Rostoker et al. | 3/1.9 |
| 4,404,684 | 9/1983 | Takada | 382/25 |
| 4,436,684 | 3/1984 | White | 3/1.9 |
| 4,506,393 | 3/1985 | Murphy | 3/1 |

Primary Examiner—Jerry Smith
Assistant Examiner—Allen MacDonald
Attorney, Agent, or Firm—Michael J. Striker

[57] ABSTRACT

A method of producing an individually adjusted endoprothesis pin includes: processing X-ray data of the bone density into a subset of tomographs showing a succession of parallel cross-sections of the bone; selecting from the subset a succession of parallel measuring planes determining from the contours of the bone cavity a structural center line and an antetortion plane of the pin; checking and adjusting desired dimensions of the pin in view of its withdrawal from the bone cavity; and machining a raw sample of the pin to form a succession of parallel disk-shaped steps corresponding in height to the spaces between the parallel planes.

9 Claims, 22 Drawing Figures

METHOD OF MANUFACTURING OF INDIVIDUALLY FORMED PROTHESIS OR IMPLANT

CROSS-REFERENCE TO RELATED APPLICATIONS.

This application is a continuation-in-part of application Ser. No. 783,794 filed Oct. 3, 1985 (now abandoned) which is a continuation of application Ser. No. 484,143, filed Apr. 8, 1983 (now abandoned).

BACKGROUND OF THE INVENTION

The invention relates to a method of producing individually formed protheses or implants and in particular, to an endoprothesis including an anchoring pin produced by the method of the invention.

Anchoring of protheses, and particularly of endoprotheses in a human bone has been a major problem in the prior art. This problem occurred with total protheses (for example, hip- head-neck-resection) and for joint-surface-substitute endoprotheses (for example, hip-, head-cap-knee slots-endoprotheses) and also for combinations of protheses (for example, upper shank part of the knee total endoprothesis).

The protheses which substitute for natural body parts vary in sizes, shapes, structures, angular positions, lengths, widths as compared to a relatively small number of filling protheses or endoprotheses, support or volume substituting parts of various materials. This means that a surgeon is in many instances, forced to adjust the bone of a patient to a prothesis model for anchoring the prothesis in the bone. In many cases this means that a bone substance should be removed for adjusting or fitting in the filling prothesis; under both conditions pressure, pulling and torsion forces which can occur on the prothesis insert or on the attachment place must be considered in the bone structure to be adjusted.

With conventional shaft-like implanted endoprotheses (for example hip endoprotheses) a relatively thin prothesis part must be anchored in a wide bone cavity. If there is spongiosa in the bone its balk or mesh structure is disturbed and its initial supporting function can not be carried out.

With conventional cement anchoring endoprotheses spongiosa is totally removed from the bone and a remaining free space formed between the prothesis and compacta of the bone is filled with special fillers, for example bone cement. In this process used for conventional total protheses and for upper surface substituting endoprotheses and the combination of those depending on implantation technique, the thickness of the cement layer, elasticity coefficient and implantation time have been found inefficient (see, for example "Bony Ingrowth Fixation of Aeetabular Components for Canine Toal Hip Replacement" by Harris, W. H., 27 Ann. Meeting Orth. Res. Sec. Vol. 6, page 74).

Tests and research have been conducted for ways of cement-free implantation possibilities which would suggest large volume prothesis shafts, longer prothesis shafts and better shaft-prothesis designs with smaller or thinner cement layers to be utilized.

This research, however, has practically failed because it is merely not possible to determine automatically when the prothesis with adjustable parts is to be used taking into consideration a real number of different lengths, widths of human joints and joint parts with use of filling and preliminarily prepared protheses.

The major problem with conventional techniques is also that eventually the endoprotheses become loosened after being inserted in place and must be readjusted. This happens with joints for total and joint surface substituting protheses and their combinations. With the upper surface substituting prothesis, important force receiving and force distributing bone structures (hard bone bark corticals) or bone mesh (spongiosa) must be removed, for example in cortical compact bone shaft tube for force receiving and force distribution and existing incongruities must be compensated by a filling material.

SUMMARY OF THE INVENTION

It is an object of the invention to provide a method of producing anatomically shaped protheses or implants and the pin structures of such protheses which make an individual adjustment of the anatomical shape of the pin of the prothesis to a bone opening possible. Only an individually anatomically shaped pin of the prothesis, particularly endoprothesis makes an optimal and reliable anchoring of the prothesis in the human bone cavity and optimal biomechanic possible.

These and other objects of the invention are attained by a method of manufacturing of three-dimensional anchoring pins of endoprotheses or implants, which comprises the following steps:

(a) measuring a patient's bone by an X-ray or nuclear spin resonance apparatus to obtain a plurality of characteristic data, such as bone density at points measured transversely to the direction of scanning movement of the apparatus, (b) processing the measured data into a set of true scale tomographs corresponding to cross-sections of the bone transverse to the scanning movement of the measuring apparatus;

(c) determining in the set of tomographs a subset corresponding to a part of the bone which will receive the anchoring pin;

(d) determining in the subset at least two centroids corresponding to planar centers of gravity at different levels in the bone part whereby a connection line of the centroids defines a structural center line of the endoprothesis;

(e) determining in the subset a succession of superposed planes extending parallel to each other and being spaced apart at distances selected in dependency on the shape of cavity of the determined bone part, and evaluating contours of the bone cavity at the parallel planes;

(f) determining desired dimensions of a contour of the anchoring pin to match the contour of the bone cavity at respective parallel planes, checking the dimensions in view of the withdrawal of the pin from the bone cavity, and readjusting the dimension to prevent collision of the pin with the contour of the bone opening during the withdrawal of the pin;

(g) storing final values of the desired pin contour dimensions;

(h) machining a raw sample of the pin in accordance with the stored final values by removing material from circumferential areas of the sample corresponding in height to spaces between the successive parallel planes in the subset of tomographs whereby the resulting step-like disks machined on the sample are oriented in accordance with said parallel planes.

The method according to the invention can be carried out automatically on industrially favorable principles with the aid of computers. Depending upon current developments of x-ray technique and nuclear spin resonance technique the method according to the invention can be carried out with a small member of process steps.

The endoprotheses produced by the method of the invention can be individually adjusted in each concrete case of use so that an anatomical optimal fit of a prothesis or of an anchoring pin of the protehesis in the bone cavity, preservation of the structure of the bone carrying the prothesis, are ensured. Thereby conditions for a lasting and effective anchoring of the prothesis are provided. The upper surface of the prothesis or the upper surface of the anchoring member can be provided with conventional prothesis coatings which, for example, favorably effect the bone growth. The upper surfaces of the protheses can be smooth or porous rough layer. According to the method of the invention, hollow prothesis-shaped members or meshed-network or plait-network protheses compatible with the spongiosa structure of the bone can be produced and protheses can be adjusted to the outer shape and structure of the bones. Various materials utilized simply or in combinations, such as metal, plastics, or ceramics, can be used.

With the protheses produced by the method of the invention the amount of bone cement is limited to minimum or its use is not required due to the fact that accurate individual anatomic shapes and lengths of the protheses are obtained as a result of the method of the invention. Furthermore, individual biomechanical and therapeutic aspects can be more effectively taken in consideration in the method of the invention.

The method according to the invention can be used for individual forms and casts of other implants, for example for breast implants and the like. Special plates, angular plates, screws, nails, rods or the like elements utilized in surgery and orthopedics permit adjusting and producing of protheses according to individual structural conditions which include dimensions, a number and distribution of anchoring openings, the length of threads and the like. The supporting plane of the plates or supporting collars of the protheses is precisely definable. Due to the accurate definition of the anchoring area of the prothesis in the bone cavity, such parameters as joint head diameter of the hip joint, shank collar length and various angular positions and articulated joint surface geometry of the other prothesis elements can be adjusted to the individual patients, for example to his or her body weight, pelvis or hip ratio, material friction ratio, lever arm ratio and size ratio.

The method according to the invention when compared to conventional methods of the type under consideration, is very inexpensive and improves quality and longevitity of endoprotheses inserted in bones.

The method according to the invention, due to the use of computers, significantly improves a safety factor. When a prothesis image is determined from the computer generated tomographs, a specialist can further define the contour shape of the prothesis.

A contour image received from the tomographs can be determined automatically by scanning, by means of light and electric beams and storage of all examination data of each process step can be provided in the computer which automatically makes from the stored data a spatious combination of the range of the contour image and in accordance with a given testing program, for example, simulated collision measurement, and makes necessary corrections and modifications of the contour image to adjust the same to the stored values. It is also possible, in the method according to the invention with an application of a computer to transmit individually determined contour image into a three-dimensional model by means of a copying member of a prothesis manufacturing machine.

The method of the invention can be applied to any material normally used for the prothesis.

With metal or plastics materials the prothesis is produced by milling, polishing, turning, electrical erosion, forging or pressing. All these processes should be performed taking into consideration the desired dimension values received from the computer or according to a three-dimensional model preliminarily produced. The diamension values can be also used for producing casting moulds for the protheses.

Individually formed protheses according to the invention are adjusted in bones in their supporting regions. In case of a joint endoprothesis, such as a joint surface substituting element or a total joint substituting element, this individual adjustment is carried out in the region of the anchoring surface and in the region of the articulated joint surface. The whole geometry of caps, cords, muscles and fibers in the joint, and also the whole "bio-mechanics" are considered in the method. Important biomechanical and therapeutic aspects, such as axes positions, lengths, sizes and radii of joint parts are also considered. The method of the invention also permits the consideration of osteogenically efficient or also impact-dampening coating of the prothesis elements. Due to the application of computers it is possible to use a available control program for determining the spatious combination of adjusted image range data of individual tomographs, and for determining a spatious combination of adjusted range data for a hollow care in the prothesis between the supporting regions.

The particular advantage of application of computers in the method of this invention resides in that the examination of load capacity of each individually formed prothesis need not be an additional processing step to be conducted on prothesis model but is performed by computer during the determination of adjusted dimensional values.

The prothesis may be produced from a blank or raw sample by removing material therefrom to produce a contour according to a desired pattern received from the examined and modified stored dimensional values from the computer.

According to further features of the invention an endoprothesis which comprises an anchoring pin to be inserted into an opening formed in a bone may be manufactured by the above-described method. The pin is formed with a plurality of superposed step-like disks, each disk having a contour individually adjusted to a respective cross-section of the bone cavity, at which the disk is located when the anchoring pin is inserted into the cavity.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENT

Figures 1, 2, 3:
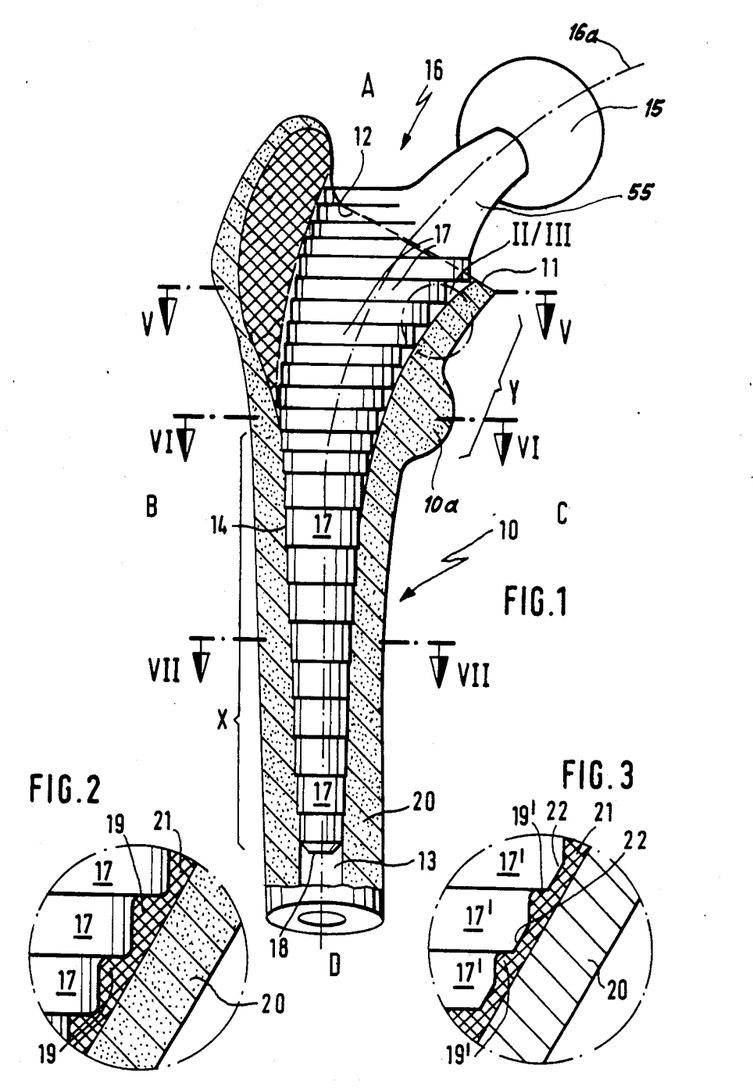
FIG. 1 is a longitudinal section through an antetorsion plane of a thigh bone with an inplanted hip joint endoprothesis.
FIG. 2 is a detailed view II of FIG. 1, shown on an enlarged scale.
FIG. 3 is modification of FIG. 2.
Figure 4:
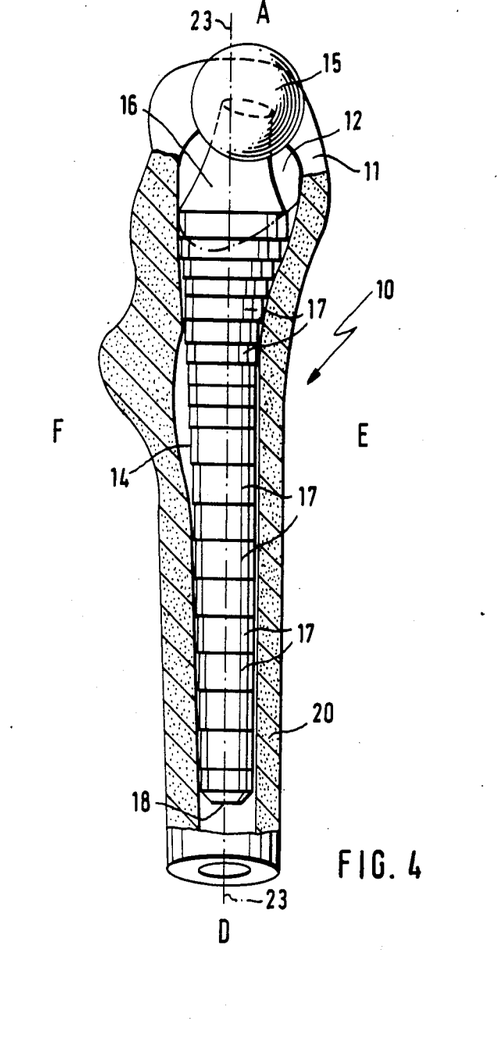
FIG. 4 is a longitudinal section of the thigh bone with the inplanted endoprothesis of FIG. 1 but turned by 90° to the antetorsion plane.

Referring now to the drawings, FIGS. 1 to 4 show sectional views of a thigh bone 10 with an anchoring pin 14 of a hip endoprothesis inserted therein. In FIGS. 1 and 4, the sides of the bone are depicted in capital letters. Reference character A designates an upper side, D identifies a bottom side, B is an outer side, C is an inner side, E denotes a front side and F designates the rear side of the thigh bone 10.

The head of the thigh bone 10 is cut off along plane 11. The resulting opening 12 opens into a bone cavity 13 produced by scraping off spongiosa from the interior of the bone and extending from the plane 11 to the bottom end of the bone. An anchoring pin 14 of the joint head 15 of the hip joint endoprothesis is inserted into the opening 12. The anchoring pin 14 which extends along a partially curved axis 16a shown with dot-dashed line, has a contour defined by a succession of setp-like disks 17, whose orientation will be described later in connection with FIGS. 8-12.

As seen in FIG. 1 step-like disks 17 positioned along the lower straight portion of axis 16a down to the bottom end of the pin have a relatively large height and, when viewed from the bottom end 18 up, they increase in diameter without any undercuts such that the pin has a funnel-like configuration. The step-like disks forming the curved upper portion of the pin 14 adjoining the curved neck 55 of the endoprothesis are reduced in height in dependency on the widening cross-section of the curved part of the bone cavity.

The contours of individual steps 17, at least in the straight supporting part X of pin 14, are adjusted to the contour of the bone cavity 13 over the whole periphery thereof.

In the upper supporting part Y of pin 14, the adjustment of the contours of steps 17 to the contour of the bone cavity 13 is limited predominanty to the concave region of the pin part Y. The upper supporting part Y extends approximately between the Adam's arc of opening 12 up to below trochanter 10a. In the convexly curved region opposite to part Y the successive step-like disks 17 form undercuts when viewed in the direction from pin end 18 toward the joint head 15. For the sake of problem free insertibility of the pin, these undercut steps do not fully engage the opposite wall portion bone cavity. In this convex region the corresponding part of pin 14 can be made without any steps in the contour.

FIGS. 2 and 3 illustrate a part of the step-like contour of pin 14 on enlarged scale. Interspace 19 between individual steps 17 and compacta 20 of the bone are proferably filled up with trabecular bones because a trabecular transition layer 21 still remains on the compacta of a thigh bone. FIG. 3 illustrates a portion of anchoring pin 14 with steps 17 which are formed with beveled corners 22, resulting in a reduced interspace 19' between individual steps 17'.

The beveled configuration of the steps of the anchoring pin makes it possible to reinsert the pin in the case of enlargement of the bone cavity resulting from bone decay due to high age for example, whereby the pin resumes its engagement with the compactar.

Figure 5:
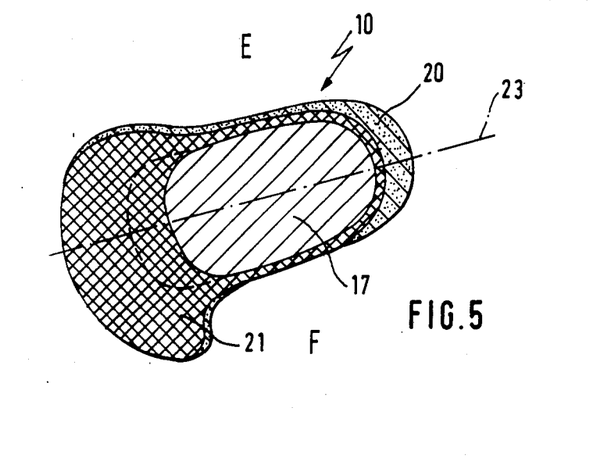
FIG. 5 is a sectional view on line V—V of FIG. 1.
Figure 6:
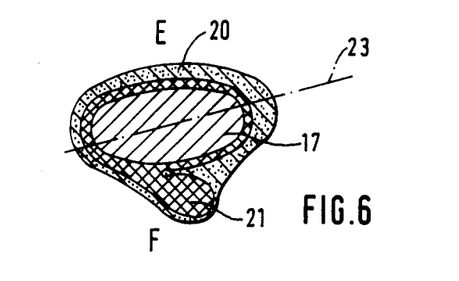
FIG. 6 is a sectional view on line VI—VI of FIG. 1.
Figure 7:
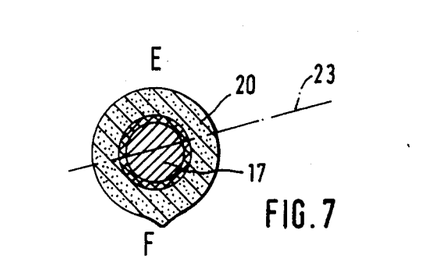
FIG. 7 is a sectional view on line VII—VII of FIG. 1.
Figure 14:
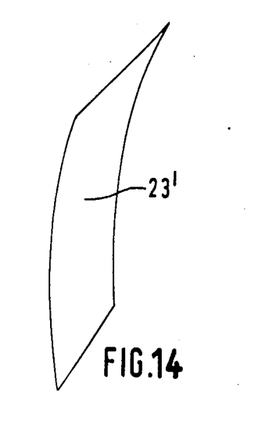
FIG. 14 shows a curved antetorsion plane.
Figure 15:
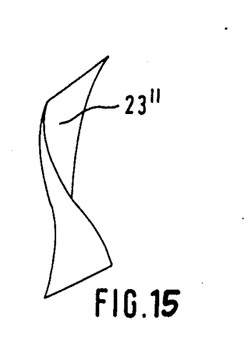
FIG. 15 shows a twisted antetorsion plane.
Figure 16:
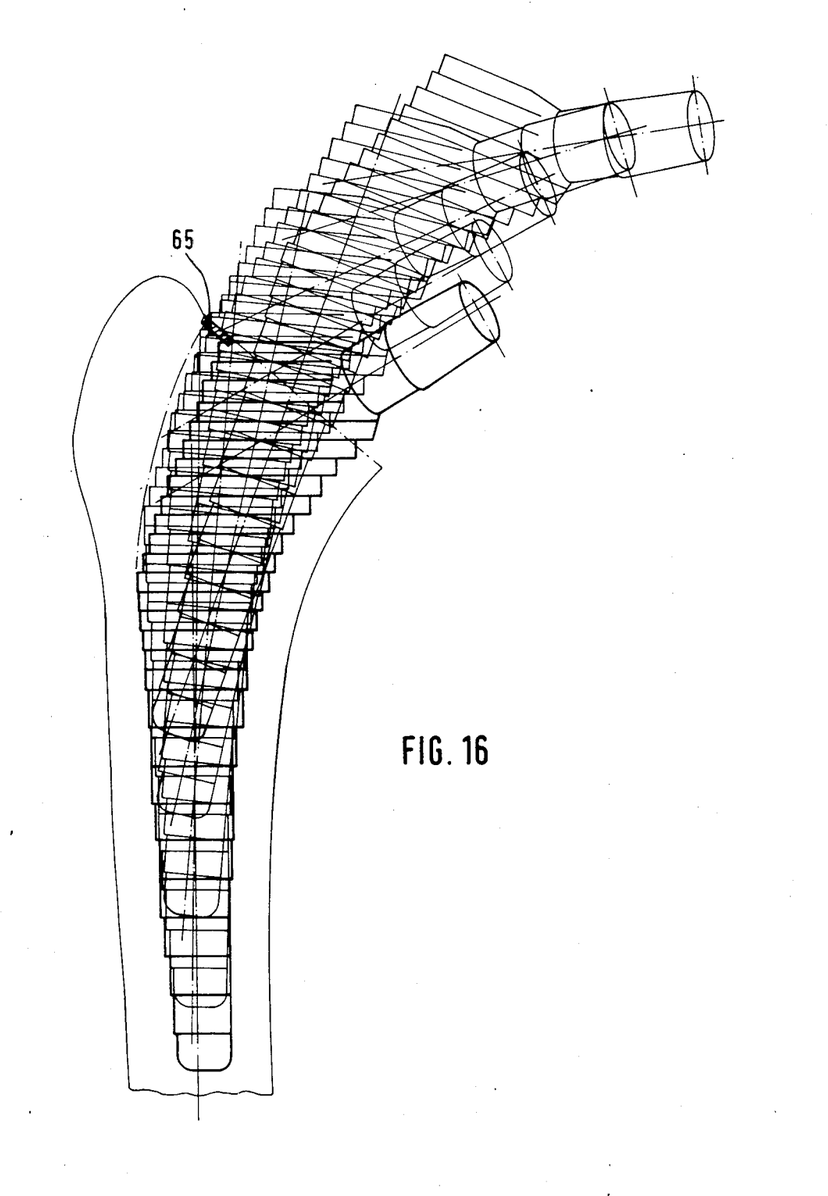
FIG. 16 shows a computer simulation of a plurality of positions of a matched anchoring pin during its insertion into or withdrawal from a bone cavity.

Transverse cross-sections shown in FIGS. 5, 6 and 7 of the thigh bone 10 of FIG. 1 illustrate an adjustment of various contours of individual step-like disks 17 of the anchoring pin to the contours of bone cavity 13. The spongiosa areas 21 and the trabecular areas are shown by cross-hatching to distinguish the same from compacta areas 20 of the bone. Line 23 in Figs. 5-7 denotes an orientation of the antetorsion plane in the respective cross-sections. The shape of anchoring pin 14 conforms to the antertorsion plane, as indicated in the implanted pin 14 in FIG. 14. A curved antetorsion plane 23' of anchoring pin 14 is schematically shown in FIG. 15. In FIG. 14 corresponding to a section of FIG. 4, the antetorsion plane 23 is a straight plane. FIG. 16 shows schematically antetorsion plane 23" which is not only curved but also twisted; the anchoring elements of the hip joint endoprothesis can be formed in accordance with the plane 23".

The novel method for an individual adjustment of an anchoring pin of the before described hip-joint endoprothesis will be described with reference to FIGS. 8-12. The first steps involve diagnosis by means of a computer enhanced tomography using X-ray or nuclear spin resonance apparatus. For example, when using an X-ray apparatus, first a density of the bone 10 is measured at a plurality of points whereby the X-ray apparatus moves along a coordinate 50, to measure bone density transversely to the path of its movement.

Figures 8, 9A, 9B:
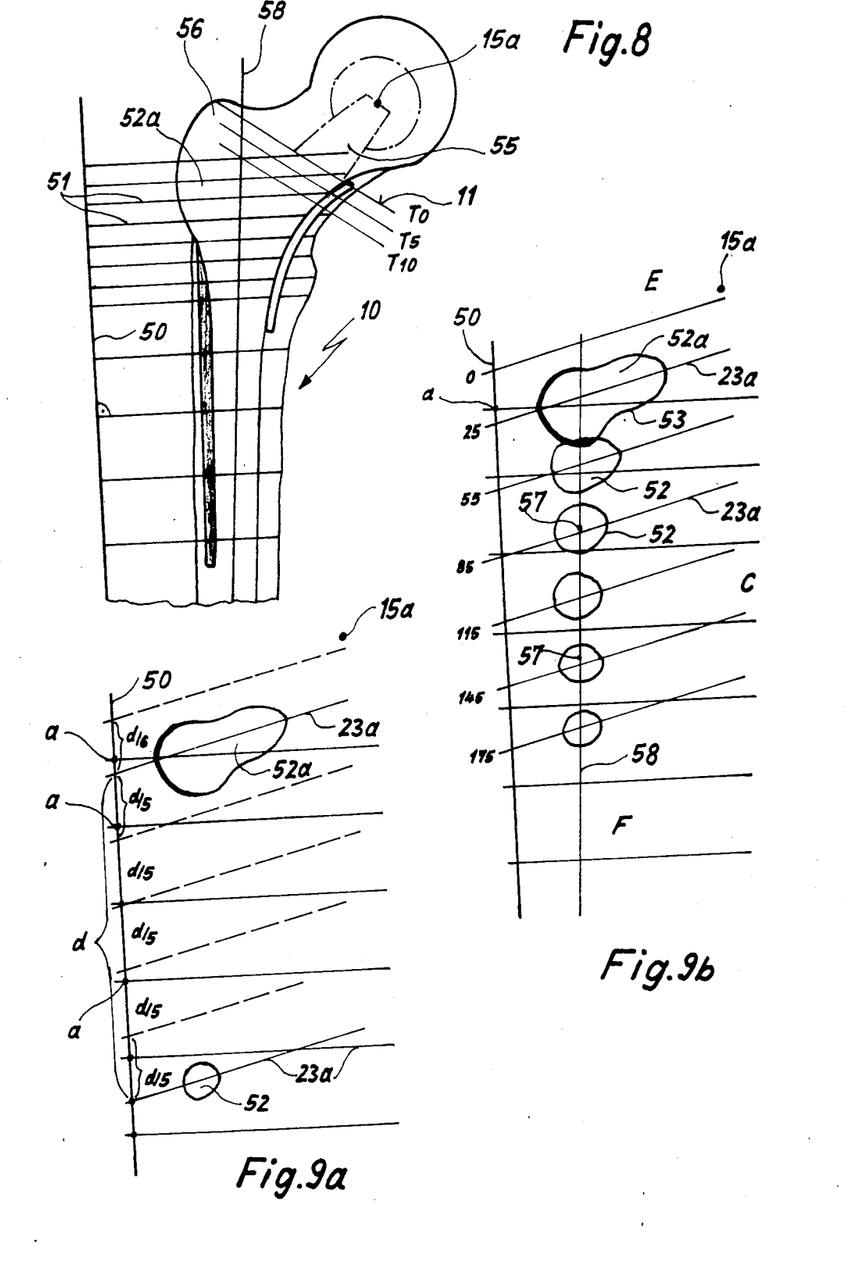
FIG. 8 is a schematic view of a part of a thigh bone joint of FIG. 1 showing a succession of parallel planes whose mutual spacing is selected in dependency on the shape of bone cavity.
FIG. 9a shows tomographs of the bone with indicated bone cavity contours whose antetorsion directions are oriented in parallel.
FIG. 9b shows the contours of FIG. 9b arranged along a structural center line.

On the basis of measured data, a computer produces a set of tomographs depicting a plurality of transverse cross-sections of the bone 10 relative to the coordinate 50. Predetermined gradation of gray in X-ray pictures correspond to correlated densities of different bone areas. From the tomographs, a subset of tomographs is selected corresponding to different parallel planes 51 whose spacing is dependent on the configuration of the bone cavity, as indicated in FIG. 8.

In the course of the data processing, the density of spongiosa to be removed from bone cavity by surgical operation is also determined, and only the density data exceeding that of the spongiosa is further processed to produce the tomographs. The higher density data correspond to the trabecular and compact bone components which are of interest for the design of anchoring pin. The remaining bone structure are substantially suppressed or blurred. As a result the tomographs 52 show the inner contour 53 of the bone 10 at the selected parallel planes 51. For further processing in the computer, each point of the contour 53 of the bone cavity is evaluated in a system of coordinates x and y. The superposed tomographs of the individual contours 53 in respective measuring planes represent a preliminary theoretical model of the bone cavity to be produced by scraping off the low density spongiosa. In order to manufacture an individually adjusted pin of the endoprothesis, the preliminary cavity shape must be corrected so as to enable a problem free insertion and withdrawal of the pin into and from the bone cavity. For this purpose, a position of center point 15a of the head of the hip-joint endoprothesis relative to the bone cavity must be determined. This position is determined by the surgeon. It can correspond to the center of natural hip joint, or can deviate from the latter, depending on therapentical and/or biomechanical or operation-technical considerations. Thereafter the length of the neck 55 of the endoprothesis is determined. The location of separation plane 11 of the bone opening as a rule is selected in dependency on the length of the neck part 55 and is aligned with trochanter point 56 (FIG. 8) and forming an angle, for instance 60°, with structural center line 58 of the pin.

Figure 9:
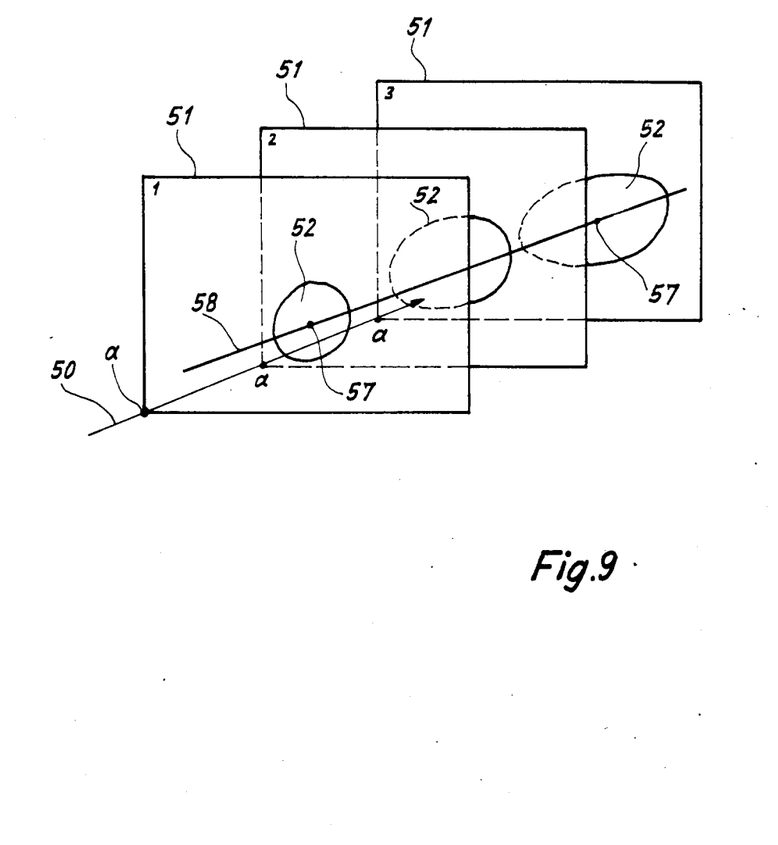
FIG. 9 shows a succession of superposed tomographic planes with indicated contours of bone cavity arranged in an antetorsion plane along a structural center line.

FIG. 9 illustrates a spatial arrangement of three tomographs 52 in successive measuring planes 51 which, as mentioned before, extend parallel to each other at right angles to the path of movement 50 of a measuring X-ray apparatus. Assuming a system of right angle coordinates x, y coinciding with the sides of respective tomographs, the path 50 represents a third coordinate z. FIG. 9 also shows a structural center line 58 defined as a connection line of two planar center of gravity points 57 of cavity contours pertaining to different measuring planes 51. The determiniation of the points 57 will be explained in connection with FIGS. 9a and 9b. The tomographs 52 pertaining to the selected measuring planes 51 are now tilted into a common plane in alignment with the coordinate z and desired dimensional data for creating a theoretical model of the anchoring pin are evaluated in this common plane. As illustrated in FIGS. 9a and 9b, a measuring plane pertaining to tomograph 52a showing a transverse cross section of the bone 10 close to an intended opening 12 into the bone cavity, is selected as a basic plane. The longest diameter of the cavity contour in the tomograph 52a (FIG. 9a) determines the antetorsion direction 23a. In the case of a straight structural center axis 58, a line 23a' is drawn parallel to the antetorsion direction in the lowermost tomograph 52 close to the center of the corresponding cavity contour. The distance of intersection points of the lines 23a and 23a' with the coordinate z (path of movement 50 of the X-ray apparatus) determines a projected total length d of the anchoring pin 14. The total length d is subdivided into sections according to selected spacings of respective measuring planes 51. The antetorsion directions 23a of all bone cavity contours on to tomographs determine the shape of the antetorsion plane 23 of the pin. In the examples of FIGS. 14 and 15, the antetorsion plane has a curved shape.

The planar centers of gravity corresponding to centroids 57 in at least two tomographs 52 which are sufficiently spaced apart (FIG. 9b) determine a structural axis 58 of the pin 14. The structural axis does not coincide with the axis of the whole thigh bone 10 nor with the coordinate 50. Accordingly, it is necessary to realign or correct preferably by a suitable computer program, the succession of tomographs 52 with the structural center axis 58, instead of the coordinate 50 (axis z).

The tomographs pertaining to the straight supporting section of the bone in which the step-like disks 17 of the anchoring pin have an approximately circular periphery, are now aligned with the above described antetorsion plane 23. The resulting supperposed contours of the tomographic bone cavity are illustrated in the plan view of FIG. 10, together with the orientation of the center 15a of the hip-joint head relative to the antetorsion direction 23.

Figures 10, 11, 12, 17:
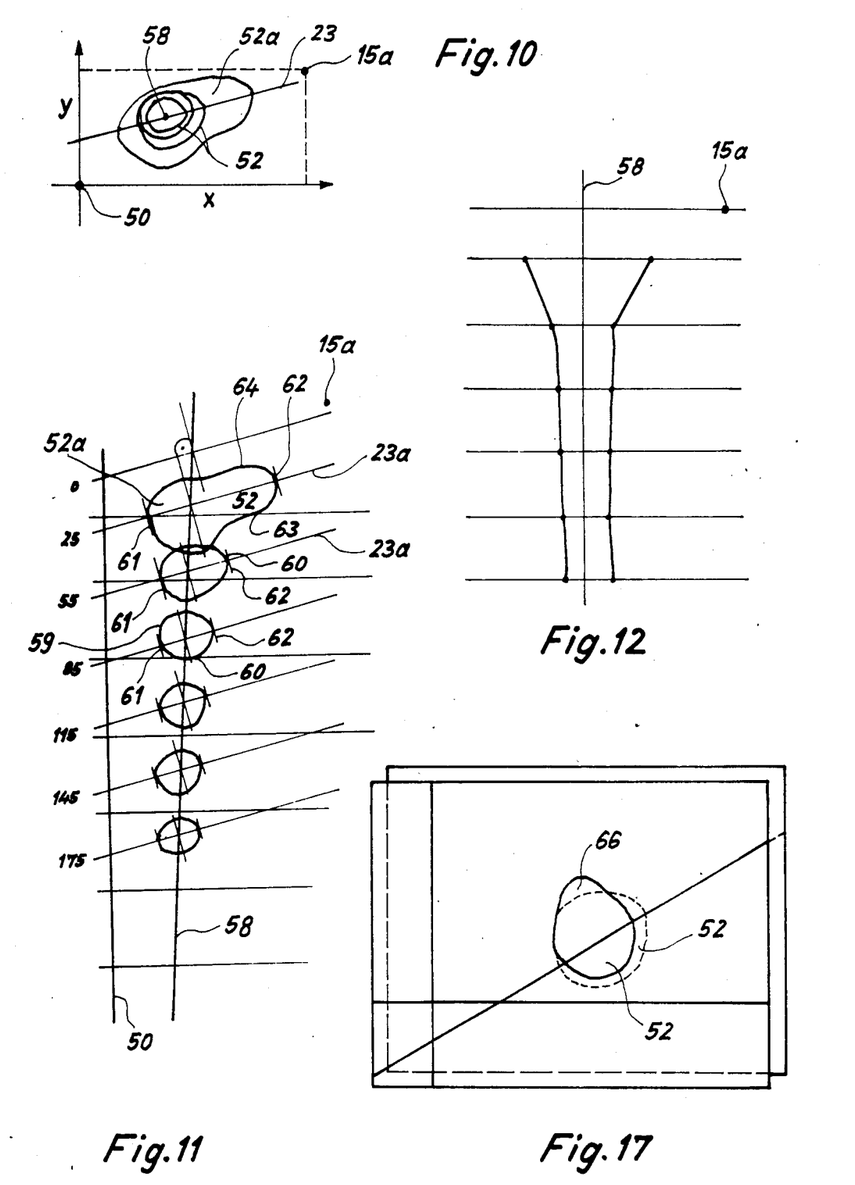
FIG. 10 is a plan view of a succession of the contours of FIGS. 9-9b.
FIG. 11 is a view similar to FIG. 9 and shown with aligned tangent lines at respective contours.
FIG. 12 is a two-dimensional representation of an anchoring pin drawn according to clearances between opposite tangent lines of FIG. 11.
FIG. 17 is a view in the direction of a structural center line of two consecutive tomographs showing an interferring overlap to be avoided.
Figure 13:
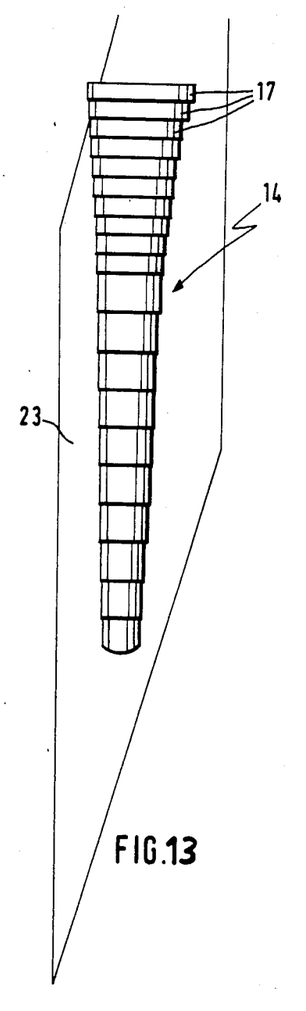
FIG. 13 shows a step-like contour of an anchoring pin according to this invention shown in a straight antetorsion plane.

Thereafter, as shown in FIG. 11, tangent lines 61 and 62 are plotted at cavity contours 53 in all tomographs 52 at right angles to corresponding antetorsion directions 23a. The spacings between two opposite tangent lines in consecutive tomographs is plotted at the distances of corresponding measuring planes symmetrically to structural axis 58, thus producing a plot diagram of a side section of a preliminary model of the anchoring pin to be produced (FIG. 12). This preliminary or theoretical model still corresponds substantially to the bone canal, is subsequently adjusted in shape in dependency on the so called collision test which is again preferably performed by means of a computer program. The collision test simulates the insertion and withdrawal of the theoretical pin into and from the theoretical bone cavity whereby an interference or collision of the pin with the rim of the bone opening 12 in plane 11 is checked. If the possibility of such a collision or of a similar interference in any of the measuring planes is detected, the dimensions of the pin and/or of the bone cavity are readjusted to eliminate the interference. In FIG. 16, a region of a possible collision between the rim of bone opening 12 and the anchoring pin is indicated by reference numeral 65. To eliminate this interference, the dimensions and mutual positioning of the step-like disks 17 in the convex part of the pin are adjusted in accordance with the left upper contour of the pin 14 shown in FIG. 1. After the collision test and the redimensioning of the pin model, the latter is checked in view of an optimum fit into the bone cavity and the corresponding adjustments are made to achieve a minimum interspace 19. In the case of a curved implantation antetorsion planes 23' and 23" (FIGS. 14, 15), adjustment of the theoretical model of the pin after the collision test also take into account the forward or backward inclination of the bone canal and also the need for rotating the pin within certain limits during insertion or withdrawal.

Finally, the model pin is checked as to its taper or conicity, that means adjustments are made to avoid undercuts or overlaps of consecutive cavity contours and corresponding steps 17 of the pin.

FIG. 17 illustrates two successive tomographs 52 displaying an undercut or overlap 66. The overlap is eliminated from the tomographs so that the bone cavity during the subsequent surgical operation be adjusted accordingly. At this stage, the theoretical models of the anchoring pin and of the bone cavity are in their final form and the completed dimensional values are stored in the computer for controlling a tool, such as an electroerosion machine for example, used in manufacturing an actual endoprothesis 16 from a raw sample 40 shown in FIG. 20.

The anchoring pin of the finished endoprothesis exhibits the characteristic step-like disks 17 (FIGS. 1 and 4) arranged in parallel planes in accordance with the measuring planes 11. If desired from the therapeutical point of view, the spacing between the measuring planes and hence the height of respective steps 17 can be selected so low that after machining the row sample, for example by a milling cutter, practically a smooth surface of the tapering, individually adjusted anchoring pin of the endoprothesis will result.

Figure 18:
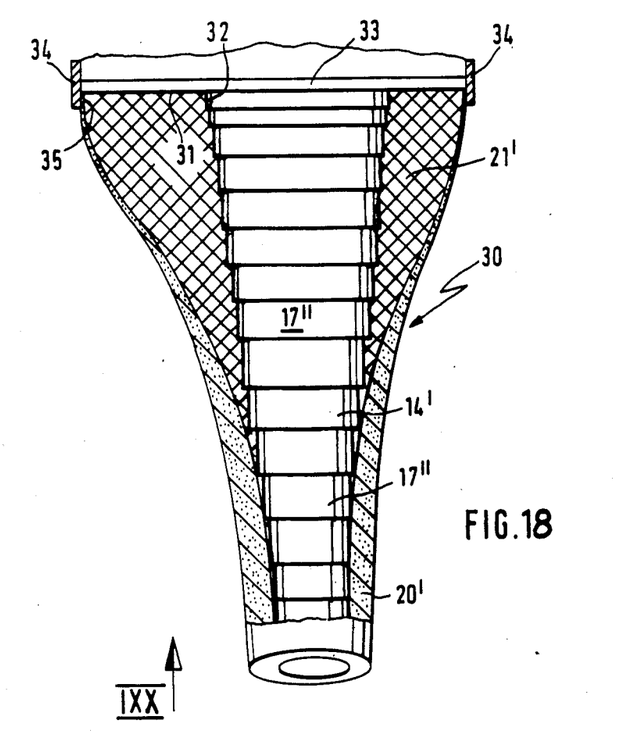
FIG. 18 is a sectional side view of a modified anchoring pin of a knee endoprothesis implanted in one end of a shin bone.
Figure 19:
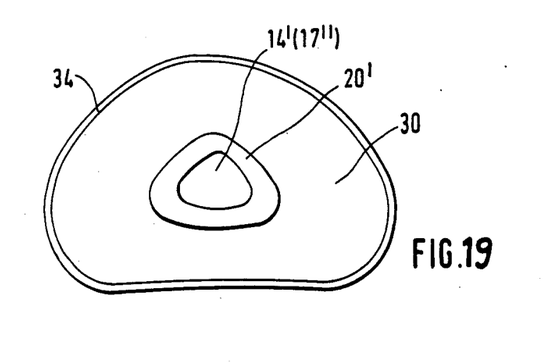
FIG. 19 is a bottom view in the direction of arrow XX of the other end of the bone of FIG. 18.

In the hip-joint endoprothesis shown in FIGS. 1 and 4, the neck 55 of the prothesis transits into the anchoring pin 14 without any collar. Consequently, there is no overhang which might hinder the insertion of the prothesis into the bone. FIG. 18 illustrates another embodiment of an endoprothesis namely a knee-joint endoprothesis which is anchored in shin bone 30. The head part of the shin bone has been severed to create a planar cut-off surface 31 provided with bone opening 32. Similarly as in the preceding example, the bone cavity for receiving pin 14' has been created by removing spongiosa 21'. The steps or steplike disks 17" of the anchoring pin 14 are again individually adjusted to match the downwardly tapering cross-section of the bone cavity and to abut directly against the compacta 20' of the bone, as indicated in FIG. 19.

The top of the anchoring pin 14" is connected to an end plate 33 which covers the entire separation surface 31 of the bone 30. The periphery of the end plate 33 is connected to a rim flange 34 which exactly follows the outer contour of the separation surface 31 of the bone and encloses the latter with an overlapping lower portion thereof. The end plate 33 together with its peripheral flange 34 thus insures the endoprothesis and its anchoring pin 14' against turning in its seat.

Figure 20:
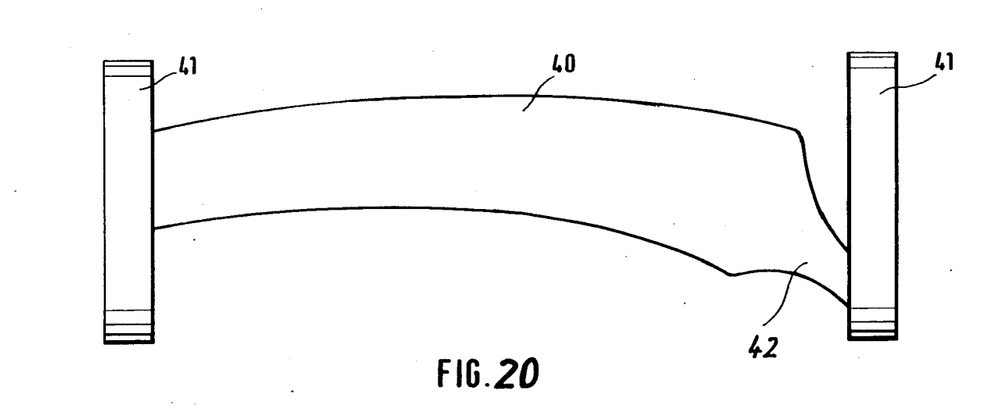
FIG. 20 is a side view of a row sample of an endoprothesis according to FIGS. 1-4.

The raw sample 40 of the endoprothesis shown in FIG. 20 can be made of titanium-or steel alloys and preshaped by forging. The ends of the raw sample are provided with two coaxial disks 41. The disks 41 serve for clamping and centering the raw sample 40 in a processing machine operating with metal removing tools. The disks 41 can be secured to the raw sample by welding, for example, or can be formed integrally therewith. After completion of the machining of the endoprothesis, the two clamping discs 41 are separated. Instead of the clamping discs the ends of the row sample 40 can be provided with centering bores.

It will be understood that each of the elements described above, or two or more together, may also find a useful application in other types of methods of producing individually formed differing from the types described above.

While the invention has been illustrated and described as embodied in a method of producing individually shaped protheses and implants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is met forth in the appended claims.

1. A method of producing an endoprothesis having an anchoring pin individually adjusted to an opening into a cavity of a bone of a patient, comprising the steps of
   (a) moving an X-ray or nuclear spin apparatus along the patient's bone and measuring transversely to the path of movement a plurality of points of the bone so as to obtain characteristic data, such as bone density, at the respective points;
   (b) processing the measured data into a set of true-scale tomographs corresponding to cross-sections of the bone in planes extending transversely to the path of movement of the X-ray or nuclear spin apparatus;
   (c) determining in the set of tomographs a subset corresponding to a part of the bone which will receive the anchoring pin;
   (d) determining in said subset at least two centroids corresponding to planar centers of gravity at different levels in said bone part whereby a connection line of said centroids defines a structural center line of the endoprothesis;
   (e) determining in said subset a succession of superposed planes extending parallel to each other at different levels, and evaluating contours of the bone cavity in said parallel planes;
   (f) determining desired dimensions of a contour of the anchoring pin to match the contour of the bone cavity at respective parallel planes, checking the dimensions in view of the withdrawal of the pin from the bone cavity, and readjusting the dimensions to prevent collision of the pin with the contour of said bone opening during the withdrawal of the pin;
   (g) storing final values of the desired pin dimensions;
   (h) machining a raw sample of the pin in accordance with the stored final values by removing material from circumferential areas of the sample corresponding in height to spaces between the successive parallel planes in said subject whereby the resulting succession of step-like disks machined on the sample are oriented in accordance with said parallel planes.

2. A method as defined in claim 1 further comprising the step of checking and modifying the dimensions of the contour of a bone cavity to be made to such an extent as to avoid overlap of said contours in the parallel planes when viewed in the direction of withdrawal of said pin.

3. A method as defined in claim 1 wherein the spacing between respective parallel planes is selected in dependency on the shape of the bone cavity in the part determined in step (c).

4. A method as defined in claim 1 for producing a hip-bone endoprothesis having an anchoring pin adjusted to the cavity of a thigh bone of a patient, further comprising the steps of
  (i) determining in the subset of tomographs after the step (e) an antetorsion direction for the pin by evaluating the largest diameter of a contour of the bone cavity in a base plane selected close to the bone opening;
  (j) determining corresponding antetorsion directions in the contours in all remaining parallel planes whereby a plane common to respective antetorsion directions defines an antetorsion plane of the pin;
  (k) determining at the contours at respective parallel planes a clearance between opposite tangential lines forming right angles with a corresponding antetorsion direction;
  (1) arrangeing the determined successive clearances of respective planes one after the other on true scale in a plan view to check the course of the bone cavity before determining the desired dimensions of the pin in step (f).

5. A method as defined in claim 1 wherein said plurality of points on the patient's bone is measured by an X-ray apparatus having screening means, the processing of measured data being made on a computer defining a limit value of density to be processed, said screening means being adjusted to screen out data of low bone density below said limit value.

6. A method as defined in claim 1 wherein said raw sample is a preliminary model and the final pin being produced by casting the machined model.

7. A method as defined in claim 1 wherein said raw sample of the pin is integrally connected between two concentric disc which after the completion of the pin are separated.

8. A method as defined in claim 7 wherein said machining step includes electroerosion.

9. A method as defined in claim 7 wherein said raw sample is produced by pressing or forgering.

* * * * *